US012635950B2

(12) United States Patent
Bremer et al.

(10) Patent No.: US 12,635,950 B2
(45) Date of Patent: May 26, 2026

(54) ANALYTE SENSOR APPLICATOR

(71) Applicant: Willow Laboratories, Inc., Irvine, CA (US)

(72) Inventors: Troy M. Bremer, Irvine, CA (US); Guy Montgomery Heaton, Mission Viejo, CA (US); Neil Martin Becker, Carlsbad, CA (US)

(73) Assignee: Willow Laboratories, Inc., Irvine, CA (US)

( * ) Notice: Subject to any disclaimer, the term of this patent is extended or adjusted under 35 U.S.C. 154(b) by 937 days.

(21) Appl. No.: 17/753,414

(22) PCT Filed: Sep. 3, 2020

(86) PCT No.: PCT/US2020/049255
§ 371 (c)(1),
(2) Date: Mar. 2, 2022

(87) PCT Pub. No.: WO2021/046255
PCT Pub. Date: Mar. 11, 2021

(65) Prior Publication Data
US 2022/0323011 A1      Oct. 13, 2022

Related U.S. Application Data

(60) Provisional application No. 62/910,701, filed on Oct. 4, 2019, provisional application No. 62/895,021, filed on Sep. 3, 2019.

(51) Int. Cl.
*A61B 5/00* (2006.01)
*A61B 5/145* (2006.01)
(Continued)

(52) U.S. Cl.
CPC ........ *A61B 5/6849* (2013.01); *A61B 5/14503* (2013.01); *A61B 5/14546* (2013.01);
(Continued)

(58) Field of Classification Search
CPC .............. A61B 5/6849; A61B 5/14503; A61B 5/14546; A61B 5/6832; A61B 50/3001; A61B 2050/005; A61B 5/14735
See application file for complete search history.

(56) References Cited

U.S. PATENT DOCUMENTS 9,084,686 B1    7/2015  McLean et al.
9,615,779 B2    4/2017  Pryor et al.
(Continued)

FOREIGN PATENT DOCUMENTS

GB        207280  A      5/1997
GB      2312932  B     12/1997
(Continued)

OTHER PUBLICATIONS

Supplemental European Search Report dated Mar. 13, 2023 for European Patent Application 20860396.9 in 8 pages.
(Continued)

*Primary Examiner* — Abid A Mustansir
(74) *Attorney, Agent, or Firm* — Knobbe, Martens, Olson & Bear, LLP

(57) ABSTRACT
An analyte sensor applicator for applying a wearable analyte monitoring device includes a housing that holds an analyte sensor assembly, a cam assembly for delivering the analyte sensor assembly, and a skin piercing for inserting a sensor, wherein the skin piercing device is retracted within the housing top after insertion.

20 Claims, 10 Drawing Sheets

(51) Int. Cl.
*A61B 50/00* (2016.01)
*A61B 50/30* (2016.01)

(52) U.S. Cl.
CPC ........ *A61B 5/6832* (2013.01); *A61B 50/3001*
(2016.02); *A61B 2050/005* (2016.02)

(56) References Cited

U.S. PATENT DOCUMENTS

| | | |
|---|---|---|
| 11,389,089 B2 | 7/2022 | Brener et al. |
| 2001/0034479 A1 | 10/2001 | Ring |
| 2002/0130042 A1 | 9/2002 | Moerman et al. |
| 2005/0149057 A1 | 7/2005 | Rathert |
| 2008/0027461 A1 | 1/2008 | Vaquero et al. |
| 2008/0195045 A1 | 8/2008 | Lanigan |
| 2010/0198934 A1 | 8/2010 | Ouchi |
| 2010/0217105 A1 | 8/2010 | Yodfat et al. |
| 2010/0286560 A1 | 11/2010 | Freeman et al. |
| 2010/0286714 A1 | 11/2010 | Gyrn |
| 2011/0061660 A1 | 3/2011 | Cruzada et al. |
| 2011/0288574 A1 | 11/2011 | Curry et al. |
| 2012/0010642 A1 | 1/2012 | Lee |
| 2012/0095406 A1 | 4/2012 | Gyrn |
| 2012/0190951 A1 | 7/2012 | Currey et al. |

| | | | |
|---|---|---|---|
| 2014/0074138 A1 | 3/2014 | Kan | |
| 2015/0273151 A1 | 10/2015 | McLoughlin et al. | |
| 2017/0112531 A1 | 4/2017 | Shoonmaker et al. | |
| 2017/0112534 A1 | 4/2017 | Schoonmaker et al. | |
| 2018/0368771 A1* | 12/2018 | Gray ................... | A61B 5/6849 |
| 2019/0133638 A1 | 5/2019 | Ii | |
| 2020/0060587 A1 | 2/2020 | Bremer | |

FOREIGN PATENT DOCUMENTS

| | | |
|---|---|---|
| JP | 2013-523216 | 4/2016 |
| WO | WO 2016/012482 A1 | 1/2016 |
| WO | WO 2016/036924 | 3/2016 |
| WO | WO 2016/130679 A2 | 8/2016 |
| WO | WO 2017/139741 | 8/2017 |
| WO | WO 2018195286 | 10/2018 |
| WO | WO 2021/046255 A1 | 3/2021 |
| WO | WO 2023/163957 | 8/2023 |

OTHER PUBLICATIONS

International Search Report and Written Opinion for PCT/US2020/049255, Dated Oct. 29, 2020 in 6 pages.

\* cited by examiner

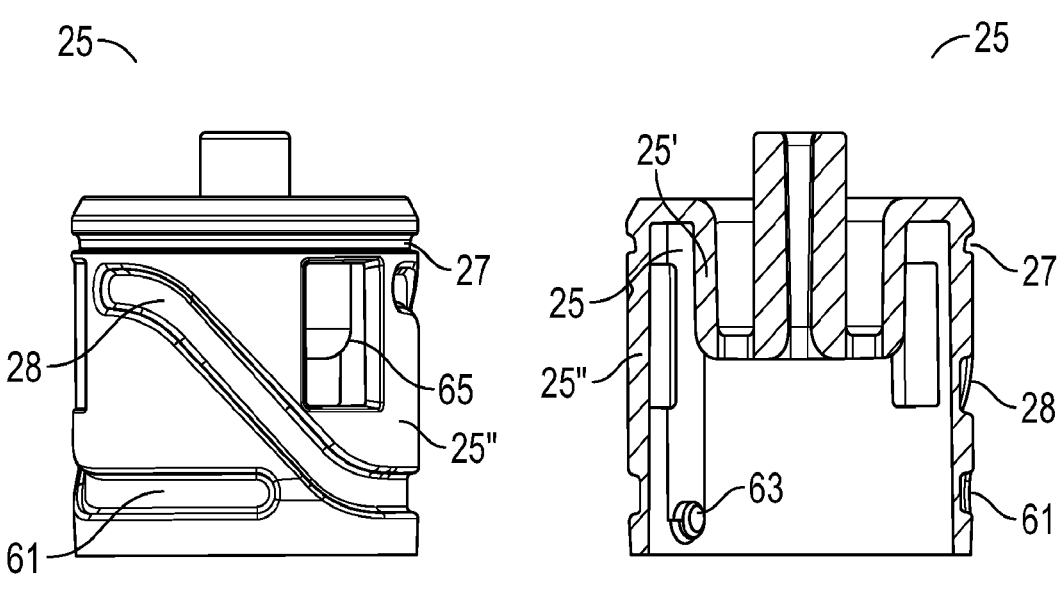
FIG. 6A FIG. 6B
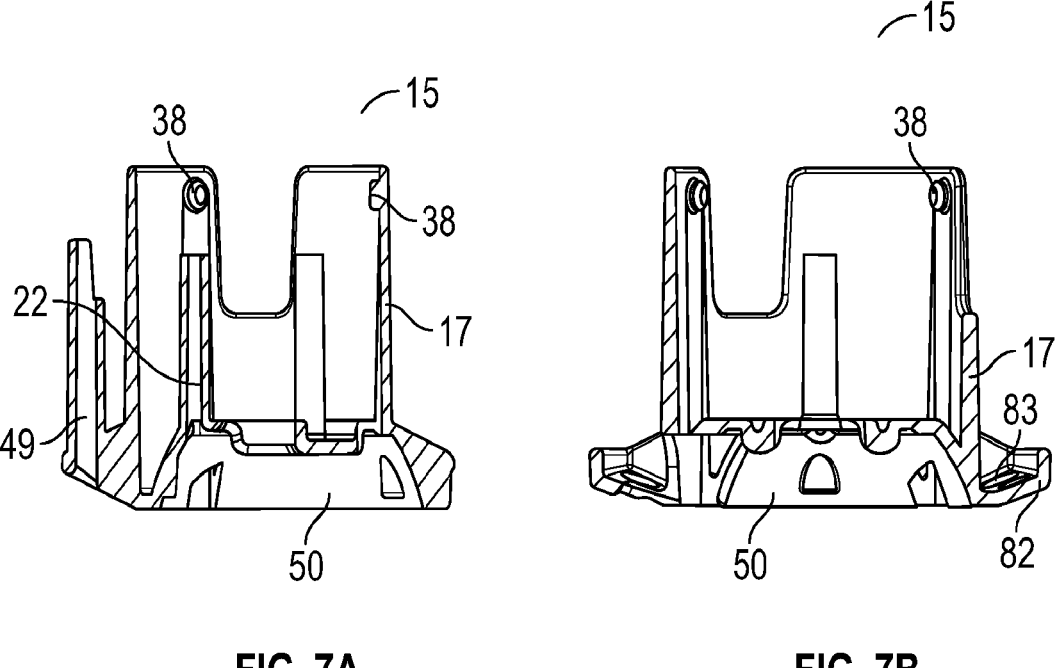
FIG. 7A FIG. 7B

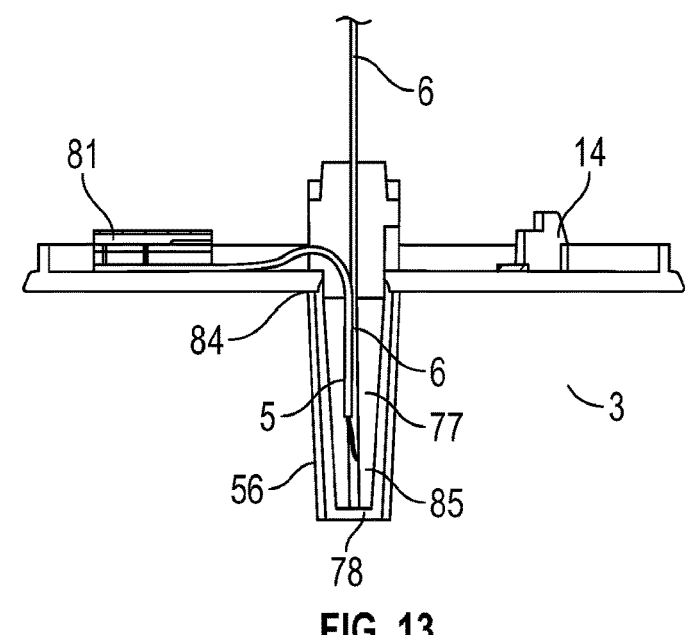
FIG. 13
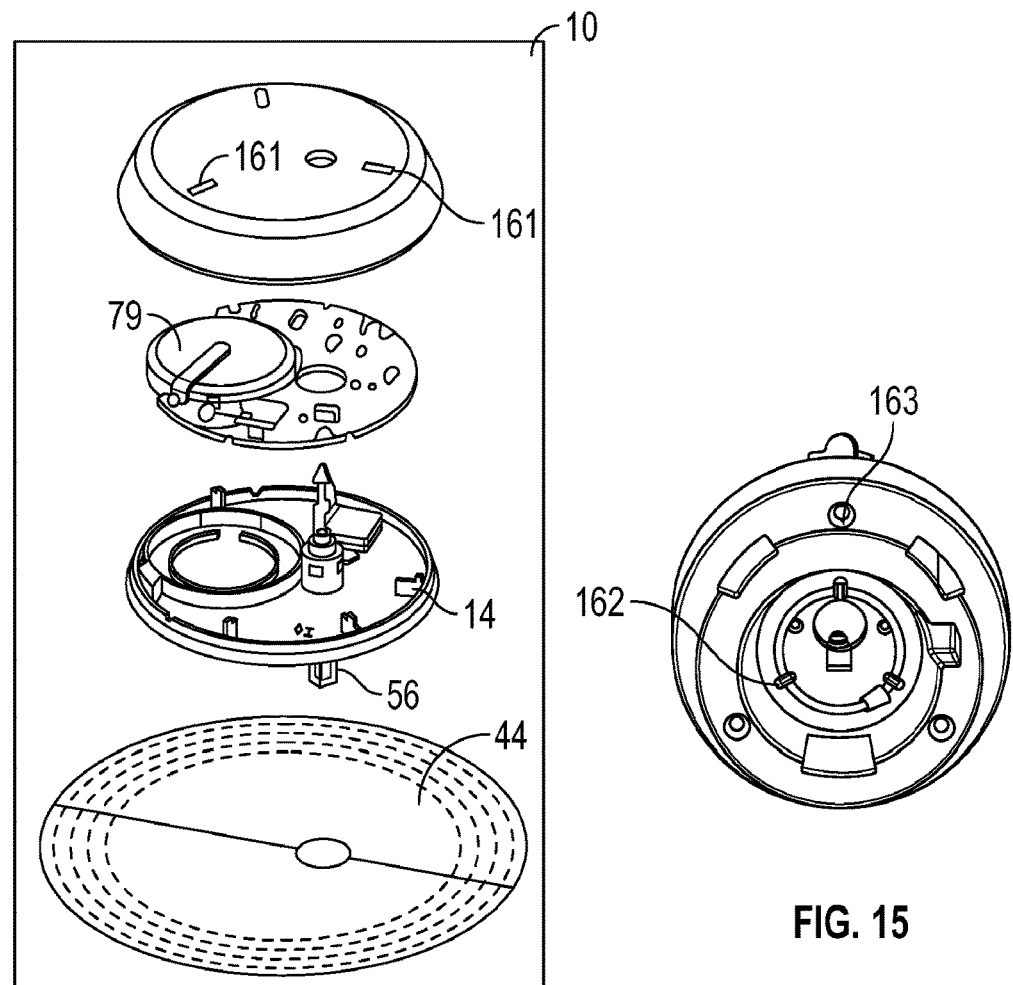
FIG. 14
FIG. 15

44

54

3

55

35

54

FINAL INSPECTION

ANALYTE SENSOR APPLICATOR

RELATED APPLICATIONS

This application claims the benefit of, and priority to, U.S. Provisional Application No. 62/895,021, filed Sep. 3, 2019 and U.S. Provisional Application No. 62/910,701, filed Oct. 4, 2019, the contents of each of which are incorporated herein by reference in their entireties for all purposes.

BACKGROUND

Analyte tracking and monitoring enable improved monitoring, diagnosis, and treatment of diseases, including diabetes. Existing methods to measure, monitor, and track analyte levels, may include sampling a bodily fluid, preparing the sample for measurement, and estimating the analyte level in the sample. For example, a diabetic may prick a finger to obtain a blood sample to measure glucose in a glucose monitoring unit. Such existing methods may be painful or inconvenient for the patient, resulting in lower compliance with physician orders to, for example, take glucose readings at certain times each day or based on patient activity. Effective monitoring, diagnosis, and treatment may benefit from analyte sensors that do not require unpleasant blood draws and/or sample preparation particularly where samples are taken multiple times each day.

Transdermally located sensing elements can be used to provide constant monitoring without requiring unpleasant blood draws to be taken multiple times a day. Inserters for delivery of a minimally invasive tissue implant applicable for biosensors, micro catheters and drug eluting implants are known. For example, an inserter for transdermally locating an analyte sensor's sensing element is disclosed in commonly owned patent application WO 2018/195286, entitled Inserter For Analyte Sensors, which is incorporated herein for all purposes in its entirety.

SUMMARY

An embodiment is directed to an applicator for a medical device. The applicator includes a housing within which a medical device, such as a wearable analyte monitoring device, is stored. The housing further comprises one or more components to affix the wearable device to the body of a user and, optionally, a sterile subassembly for insertable parts.

In one embodiment, an analyte sensor applicator includes a cam assembly comprising a cam, a piston and a retractor. The cam converts rotary motion into linear movement of the piston and retractor along an axis of insertion. The piston comprises a piston base that secures the wearable analyte monitoring device against the skin of a user, while preventing rotation and/or sliding upon retraction of a skin piercing element. The skin piercing element, such as a lancet, transdermally delivers the insertable portion of the sensor and is coupled to the retractor. After transdermal delivery of the sensor, the lancet is extracted and automatically retracted through an opening in the piston base to an unexposed position between the piston base and the housing after for safe disposal by the user.

Known analyte sensor applicator systems are typically provided as a two-part system requiring assembly of separately stored, sterile insertable components, and the applicator. Described herein, an analyte sensor applicator is provided requiring no assembly by the user. A sterile subassembly is provided by which the insertable parts are maintained within a sterile environment and incorporated into the housing during the manufacturing process. The insertable parts are contained within a sealed chamber joined to the wearable device, and after sterilization, the subassembly and remaining components are assembled within the applicator housing forming the final analyte sensor applicator assembly. The analyte sensor applicator may further comprise a detection mechanism to confirm a sterile environment has been established prior to final assembly. Moreover, a system and non-invasive method to inspect the sterile subassembly contained within a sealed housing to confirm non-breach of the sterile environment during final assembly, packaging, transport and the like, is provided.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components unless context dictates otherwise. Note that the relative dimensions of the following figures (FIGS.) may not be drawn to scale.

FIGS. 6A and 6B depict a side view and a cross sectional view of one embodiment of an applicator cam.

FIGS. 7A and 7B depict cross-sectional views of one embodiment of an applicator piston.

FIG. 13 is cross-section view of a portion of a wearable analyte monitoring device and a sterile subassembly.

FIG. 14 is an expanded view of an embodiment of a wearable analyte monitoring device and sterile subassembly.

FIG. 15 is a bottom perspective view of a piston base for engaging with an embodiment of a wearable analyte monitoring device, having an inspection port.

3

Figures 16A, 16B:
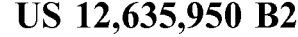

FIGS. 16A and 16B are cross-sectional views of an embodiment of an applicator and sterile assembly at two positions.

Figure 17A:
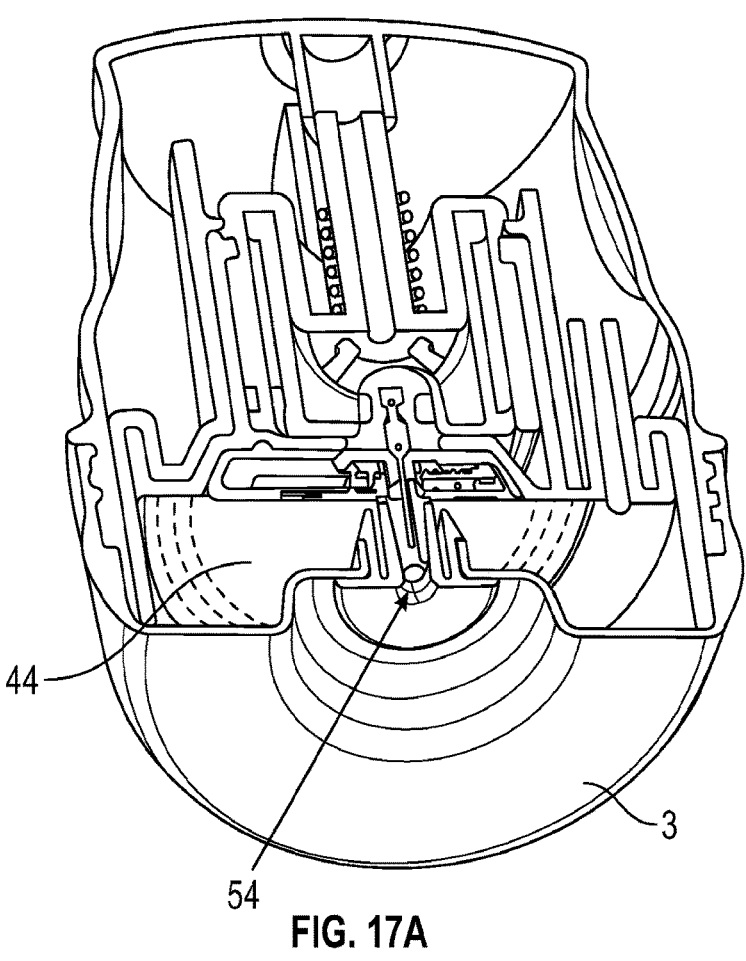
Figure 17B:
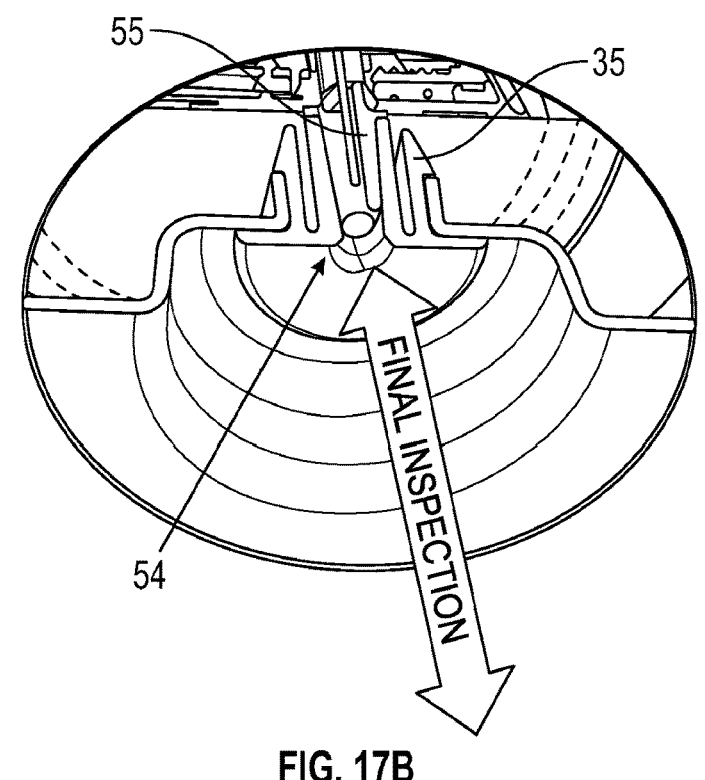

FIGS. 17A and 17B are section views of an embodiment of a wearable analyte monitoring device with a sterile subassembly within an analyte sensor applicator at two different angles.

DETAILED DESCRIPTION

It is to be understood that the embodiments of the invention described herein are not limited to particular variations set forth herein as various changes or modifications may invention. As will be apparent to those of skill in the art upon reading this disclosure, each of the individual embodiments described and illustrated herein has discrete components and features that may be readily separated from or combined with the features of any of the other several embodiments without departing from the scope or spirit of the embodiments of the present invention. In addition, many modifications may be made to adapt a particular situation, material, composition of matter, process, process act(s) or step(s) to the objective(s), spirit or scope of the embodiments of the present invention. All such modifications are intended to be within the scope of the claims made herein.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present. It will also be understood that, although the terms first, second, etc. may be used herein to describe various elements, these elements should not be limited by these terms. These terms are only used to distinguish one element from another. Thus, a first element could be termed a second element without departing from the teachings of the present invention.

Language of degree used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within less than or equal to 10% of, within less than or equal to 5% of, within less than or equal to I % of, within less than or equal to 0.1% of, and within less than or equal to 0.01% of the stated amount. If the stated amount is O (e.g., none, having no), the above recited ranges can be specific ranges, and not within a particular % of the value. Additionally, numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth.

Some embodiments have been described in connection with the accompanying drawings. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like, in connection with various embodiments can be used in all other embodiments set forth herein. Additionally, it will be recognized that any methods described herein may be practiced using any device suitable for performing the recited steps. While a number of embodiments and variations thereof have been described in detail, other modifications and methods thereof using the same will be apparent to those of skill in the art. Accordingly, it should be understood that various applications, modifications, materials, and substitutions can be made of equivalents without departing from the unique and inventive disclosure herein or the scope of the claims.

All existing subject matter mentioned herein (e.g., publications, patents, patent applications and hardware) is incorporated by reference herein in its entirety except insofar as the subject matter may conflict with the present disclosure (in which case what is present herein shall prevail).

Embodiments of the disclosed and described technology relate to applicators that may be used to deliver components of a medical device transdermally. Example medical devices that can be used with the disclosed and described technology include, and are not limited to, body wearable devices such as analyte sensors, pumps for the delivery of therapeutic drugs (insulin, chemotherapy drugs, etc.), and any other device as will be readily understood by those of skill in the art. Example medical device components that can be delivered transdermally with the embodiments disclosed and described herein include, and are not limited to, analyte sensing elements, drug delivery cannulas (micro catheters) or other delivery lumens for infusion pumps to deliver, for example, insulin and other therapeutic agents/treatments to a patient, etc. Additional items can be delivered with the embodiments disclosed herein including, and not limited to, drug eluting implants. For analyte sensors, analytes that can be measured using the embodiments of the invention disclosed and described herein include, and are not limited to, glucose, galactose, fructose, lactate, peroxide, cholesterol, amino acids, alcohol, lactic acid, and mixtures of the foregoing.

Analyte sensors, and components thereof, that may be used with the embodiments of the disclosed and described technology include, and are not limited to, those described in the following commonly assigned U.S. patents and patent applications: U.S. Pat. Nos. 7,146,203; 9,357,952; and 8,543,182, entitled "IMPLANTABLE BIOSENSOR AND METHODS OF USE THEREOF," filed Dec. 16, 2004, Sep. 23, 2013 and Jun. 29, 2006, respectively; U.S. Pat. No. 10,695,000, entitled "SYSTEMS AND METHODS FOR CONTINUOUS HEALTH MONITORING USING AN OPTO-ENZYMATIC ANALYTE SENSOR," filed Sep. 1, 2016; U.S. patent application Ser. No. 15/754,271, entitled "SYSTEMS AND METHODS FOR CONTINUOUS HEALTH MONITORING USING AN OPTO-ENZY-MATIC ANALYTE SENSOR," filed Feb. 21, 2018; U.S. patent application Ser. No. 16/490,118, entitled "ANALYTE SENSORS AND METHODS OF MANUFACTURING ANALYTE SENSORS," filed Feb. 28, 2018, and the contents of each of the above-identified patents and patent applications are incorporated herein by reference in their entireties for all purposes.

Figure 1:
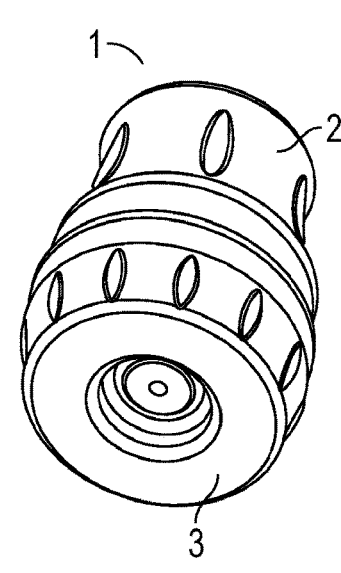
FIG. 1 is a perspective view of an analyte sensor applicator according to one embodiment.
Figure 2:
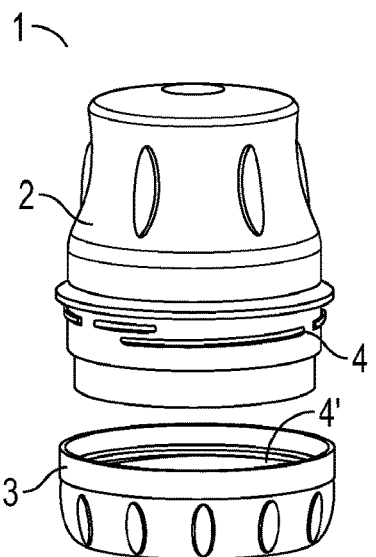
FIG. 2 is a perspective view of an analyte sensor applicator housing top and bottom parts according to one embodiment.

FIGS. 1 and 2 depict an embodiment of an analyte sensor applicator for transdermally inserting an analyte sensor tip in a user and for externally applying a wearable analyte monitoring device. An analyte sensor applicator 1 comprises a housing top 2 and housing bottom 3 that may be secured together, for example, by mating threads 4, 4'. A wearable analyte monitoring device 10 may be stored within an airtight housing chamber to reduce contamination of sensing components stored therein from exposure to air.

Figure 3:
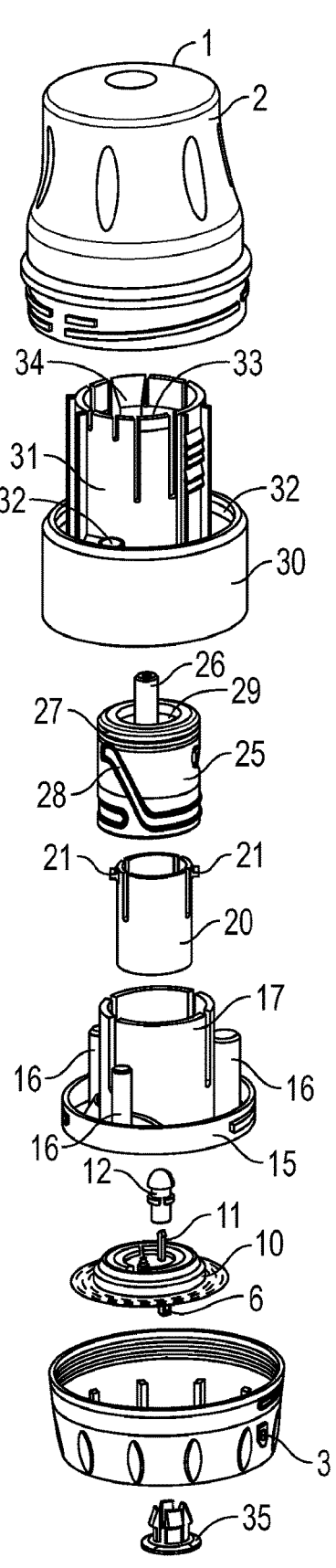
FIG. 3 depicts an expanded view of components of one embodiment of an analyte sensor applicator and analyte sensor device.

Analyte sensor applicator 1 may also include a skin-piercing device 6 that engages with an insertable portion of a sensor. Components and assemblies to deliver, secure and inspect, the wearable analyte monitoring device 10, are depicted in the expanded views of FIGS. 3, 4A and 4B.

Within the applicator housing top 2 an applicator frame 30, an applicator piston 15, an applicator cam 25, and an applicator retractor 20 are disposed. The wearable analyte monitoring device 10 connects to the retractor 20 by the applicator chuck 12 that engages with a receiving part on the bottom of the retractor 20. The applicator chuck 12 and a top portion 11 of a skin-piercing device, such as a lancet, may be connected via a snap-fitted, welded, or glued connection. The applicator chuck 12 is connected to the retractor 20, which retracts the lancet away from the user and into the housing after insertion. The connection between the chuck 12 and the retractor 20 may be via snap-fit, press-fit, or adhesive engagement, with a receiving component 57 within, or on the bottom of, the retractor 20.

Figures 5A, 5B:
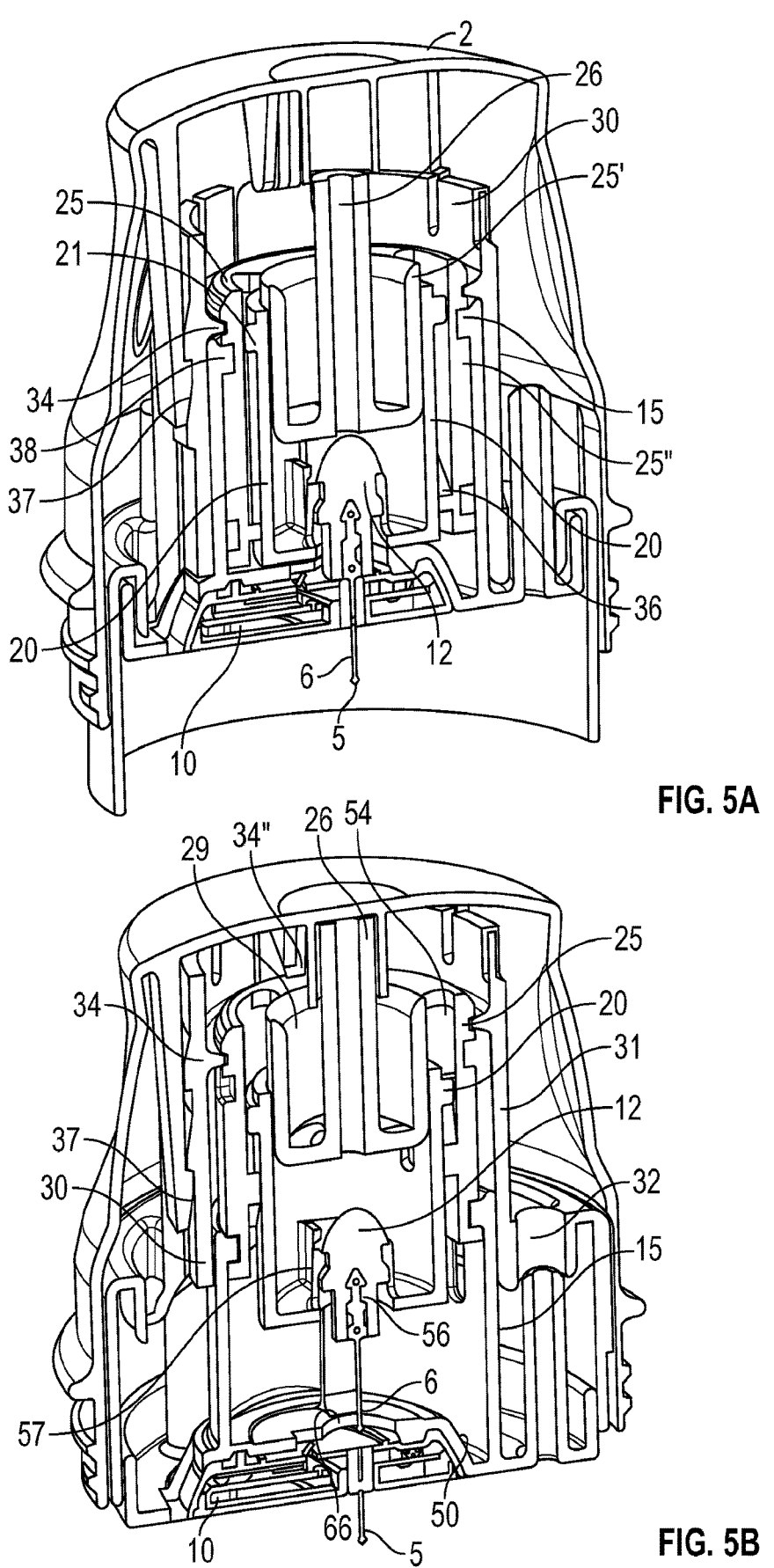
FIGS. 5A and 5B depict cross sectional views of one embodiment of an analyte sensor applicator prior to insertion of a skin piercing component and after insertion of the skin piercing component, respectively.
Figure 8A:
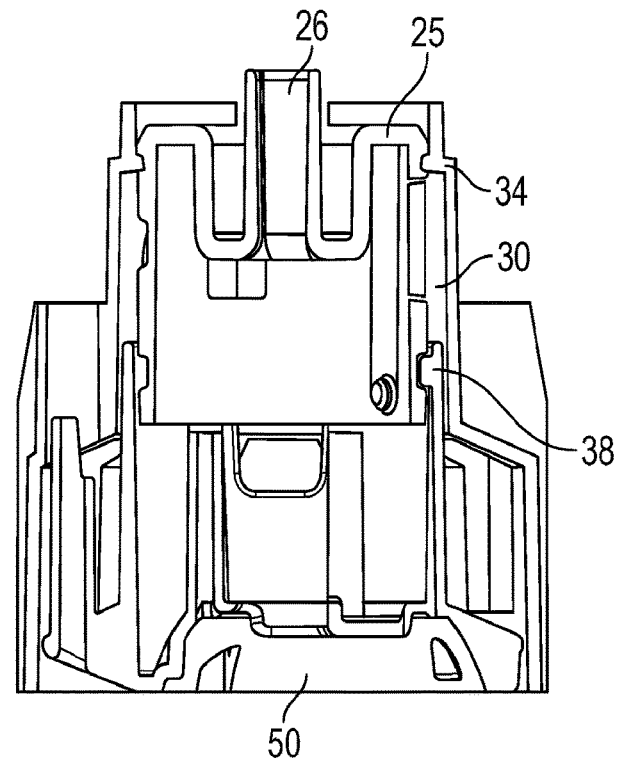
FIGS. 8A and 8B depict cross-sectional views of one embodiment of components of an applicator.
Figure 8B:
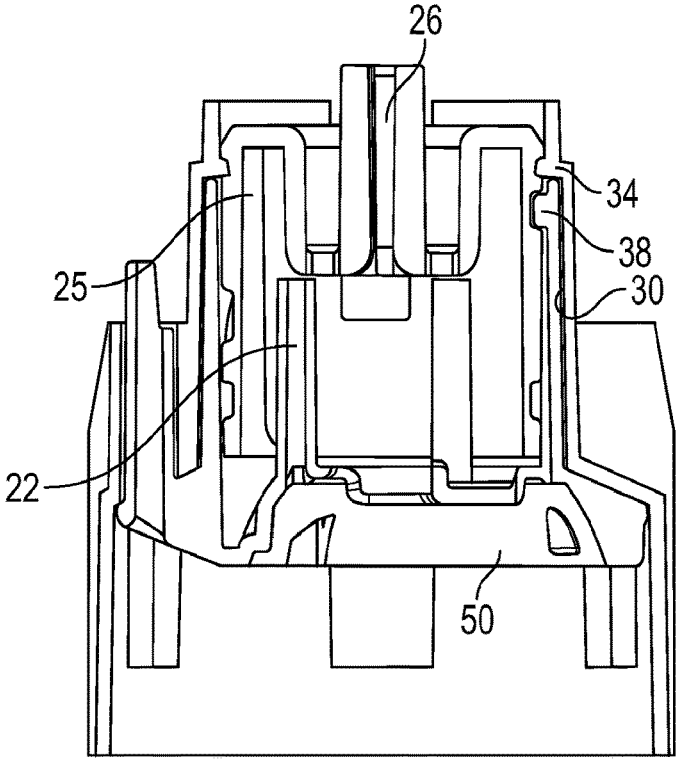
Figures 9, 10:
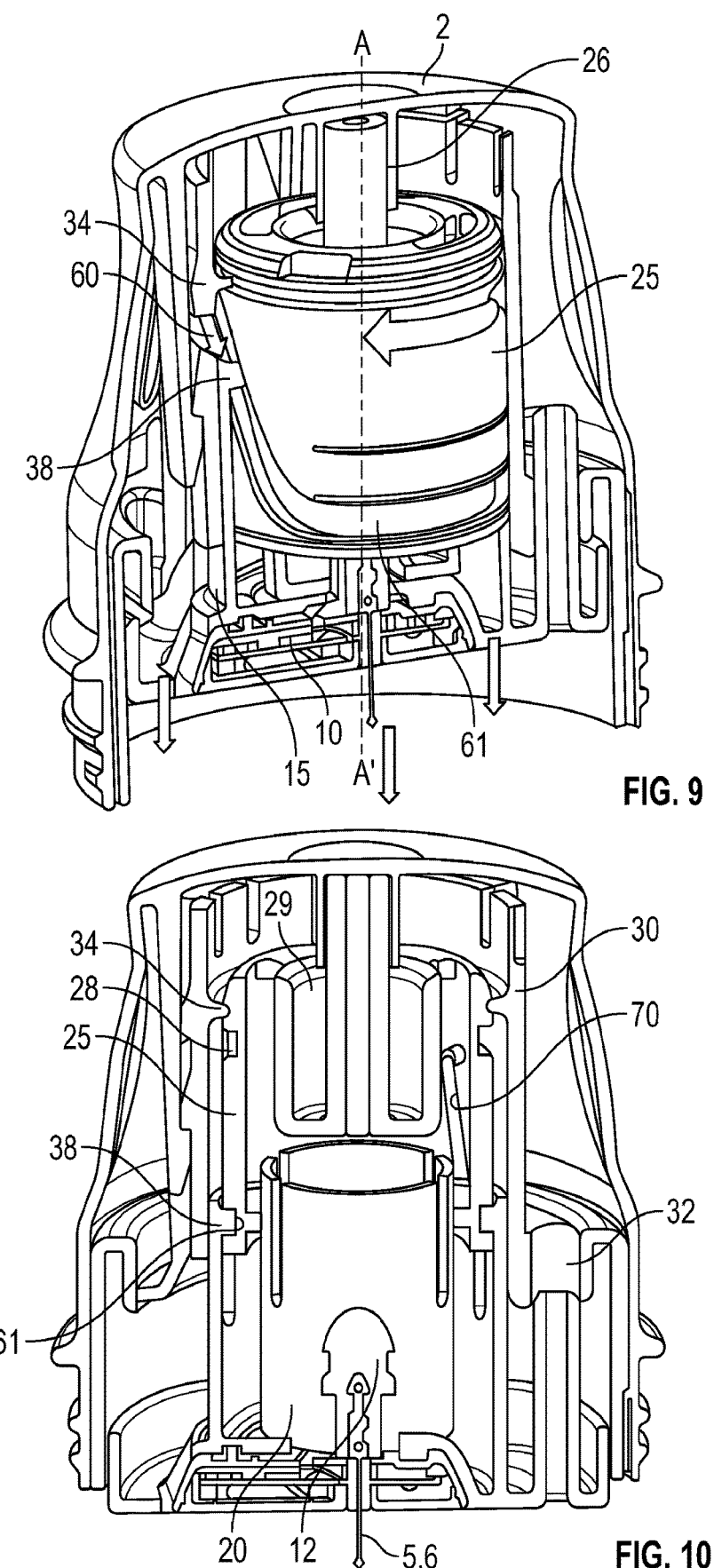
FIG. 9 depicts a partial section view illustrating position and movement of an embodiment of a cam assembly and wearable device prior to insertion of a skin piercing component.
FIG. 10 depicts a partial section view illustrating position of an embodiment of a cam assembly and wearable device after insertion of a skin piercing component.
Figure 11:
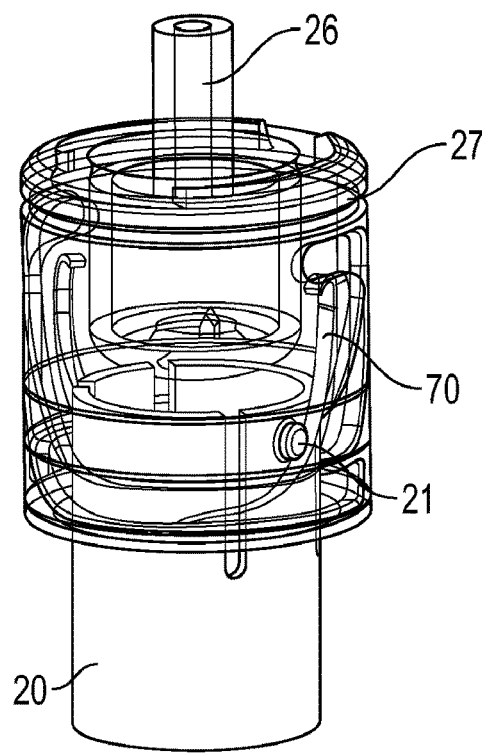
FIG. 11 illustrates one embodiment of a retractor in a distal position partially within a cam.

In the embodiment of FIGS. 5A and 5B, a cam assembly is illustrated comprising cam 25, retractor 20 and piston 15. In this embodiment, the cam assembly comprises a double walled barrel cam 25 having internal 25' and external 25" cam walls, and internal 36 and external 28 grooves on the cylindrical cam surfaces. The cam 25 is configured to align within the applicator piston 16 and the piston 15 slidably engages with external grooves 28 of the cam 25 via piston pins 16. The retractor 20 is configured to align within the cam 25 and has external retractor pins 21 to slidably engage with internal cam grooves.

Figures 4A, 4B:
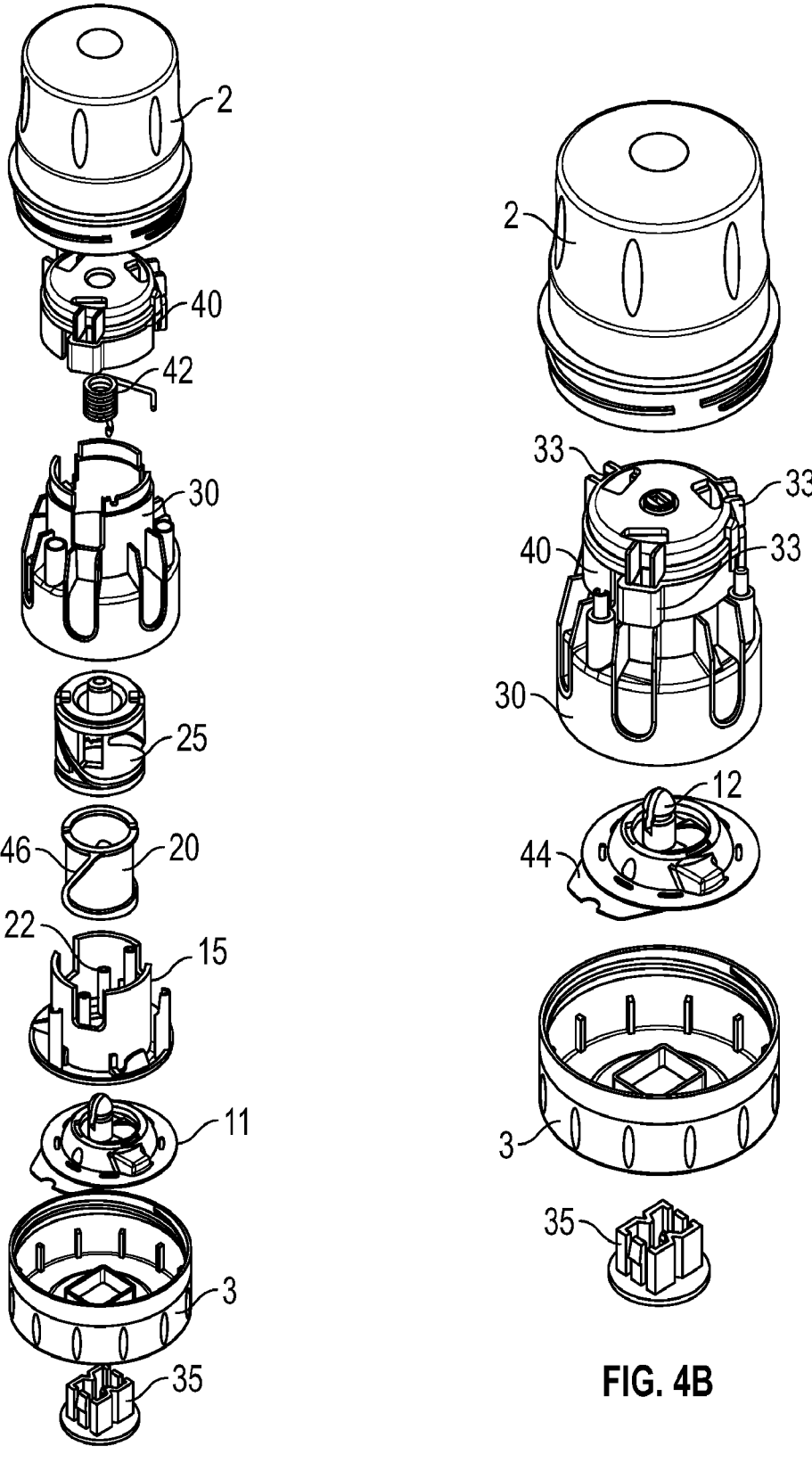
FIG. 4A is an expanded view of another embodiment of an analyte sensor applicator and analyte sensor.
FIG. 4B is a partially expanded view of an embodiment of an analyte sensor applicator and analyte sensor.

In one embodiment, components of the applicator engage in a snap-fit arrangement. The applicator frame 30 comprises openings 32 configured to receive piston arms 49 and an open center frame portion 31 configured to receive the piston cylinder 17 for alignment of the piston 15 within the applicator frame 30. The retractor 20 is aligned between internal 25' and external 25" cam walls, and the cam 25 and retractor 20 align within the piston cylinder 17. In the embodiment of FIGS. 4A and 4B, piston 15 comprises inner piston pins 22 that align with openings in the bottom of retractor 20 to prevent rotational movement of the retractor during insertion and retraction.

The housing top comprises mechanical connections such as tabs or cantilevered (e.g. 37) to engage applicator frame 30, cam 25 and optionally, the piston 15. The cam comprises a circumferential groove 27 adjacent the top of the cam that engage with one or more internal tabs 34 within the applicator frame 30.

In one embodiment, a spring, such as a torsion, tension or compression spring is positioned between the cam and the housing top under a load that releases upon pushing down on the housing top. In one embodiment, a spring positioned in a spring cavity 29 around the cam shaft 26 comprises a first end that engages with the cam 25, for example, by wrapping around a hole 89 in the bottom of the cam. A second end of the spring engages with a notch 80 on an upper portion of the applicator frame 31. An uncompressed spring may be placed under load by rotating the cam shaft 26 to wind the spring. The applicator 1 may be activated by pressing on the housing top 2, disengaging mechanical connections that lock the cam 25 to prevent rotation. Disruption of the connection between the applicator frame and the housing top to unlock the cam and activate movement of component parts may be by a displaced cantilevered pawl, a pivoting release, twisting release or rotating release. For example, where the housing top engages with slots on the frame, for example, via a cantilevered pawl, the connection may be broken where the pawl is pulled back under tension by pushing, twisting or rotating motion of the housing top, releasing the cam.

In one embodiment, illustrated in FIGS. 4A and 4B and FIGS. 16A and 16B, a frame cap 40 is provided that engages with the top of frame 30. The housing top 2 comprises one or more locking features 88 (e.g., a wedge feature) that engage with a receiving component 33 in frame cap 40, while receiving component 33 engages with frame 30 and are engaged within one or more slots 65 in the wall of cam 25 to prevent movement of cam 25 under load. Downward pressure on the housing top 2 disengages the connection between the frame cap and cam. Housing top 2 locking features 88 apply outward pressure on the frame 30 and frame cap 40, releasing frame cap receiving component 65 from the slots in the wall of the cam.

In one embodiment, a spring 42 is pre-wound or otherwise stored in the applicator under load. In another embodiment, the spring may be wound externally by the user prior to use. A winding key or knob provided, for example, on the external surface of the housing top 2 that connects internally to the cam shaft 26, maybe twisted or rotated to rotate the cam and tighten the spring. In other embodiments, an electrical release or compressed air may be used to in place of a spring to apply pressure to the rotating part.

As illustrated in FIGS. 6A, 6B, 7A, 8B, and 9 through 11, rotational movement of the cam 25 is converted to linear movement of the piston 15. As piston pins 38 follow an external cam groove 28 (directionally depicted by arrows 60) and the piston 15 moves distally, parallel with an axis of insertion (line A-A') to drive the skin-piercing device and senor into the skin. In one embodiment, the piston 15 remains in the distal position as piston pin 38 engages with a groove 61 at the bottom of the cam 25 in a locked position during retraction of the lancet by the retractor. Optionally, a catch or stop may be present on the piston rim to hold the piston to the frame and lock the piston in place in the distal position.

As depicted in in FIGS. 6A, 6B, 7A, 8B, and 9 through 11, rotational movement of the cam 25 is also converted to linear movement of the retractor 20. In one embodiment, retractor pins 21 engage groove 70 on the internal cam surface. The retractor 20 moves in the distal direction during insertion, and a subsequent, proximal movement of the retraction 20 retracts the skin-piercing device 6 after insertion.

The slope and shape or pattern of external and/or internal grooves on the cam may be varied to increase or decrease the speed or force at which the piston or retractor move up or down, or to select the number of times either part moves up or down, or whether or not either part moves up or down. In one embodiment, the piston and the retractor may be designed to move independently of the other.

As illustrated in FIGS. 7A and 7B, piston 15 comprises a concave base 50 that conforms with the geometry of the outwardly facing surface of the wearable device. As illustrated in FIGS. 4A and 4B, prior to activation, the wearable device 10 is contained within a concave portion of the piston base 50 within the housing top 2. During insertion, the piston 15 moves along the axis of insertion to drive the insertable portion 5 of the analyte sensor into the user's skin. After insertion, the piston 15 locks into a distal position to secure the wearable analyte monitoring device 10 against the skin of a user to prevent sliding or twisting upon independent retraction of the skin-piercing device by the retractor. After insertion, the skin piercing device 6 is retracted through a hole 66 in the piston base 50 and secured within the housing top 2 behind the piston base 50 to prevent injury to the user.

Figure 12:
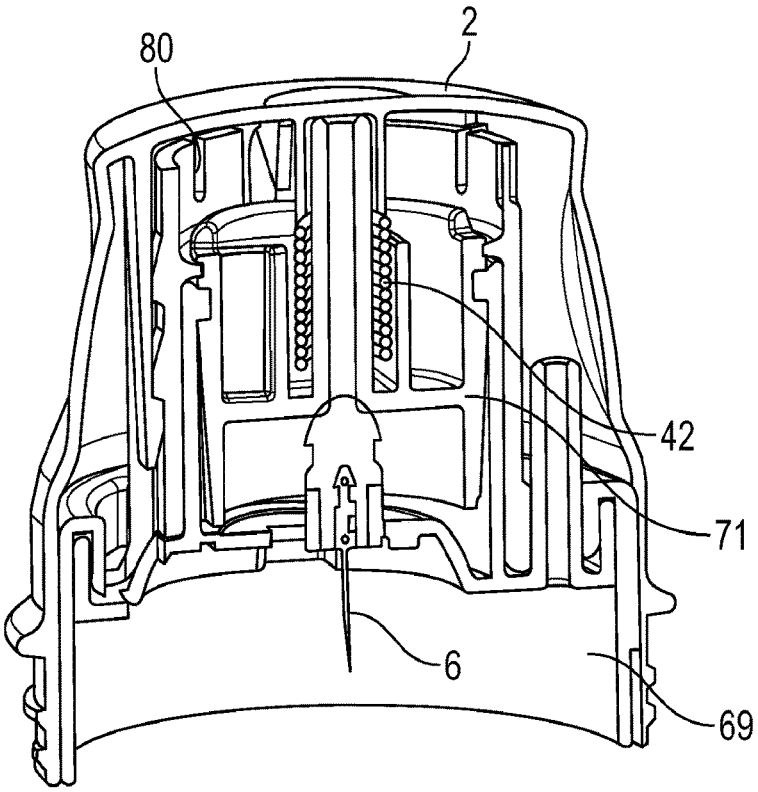
FIG. 12 depicts a cross sectional view of an analyte sensor applicator showing an exposed skin piercing component after insertion and retraction.

By comparison, in an insertion device illustrated in FIG. 12, both the piston 15 and lancet 6 are retracted in the housing 69. Where the piston does not have a base the lancet 6 is not secured behind the piston base and remains exposed, leaving the user vulnerable to injury.

Prior to activation of the device and insertion, the wearable analyte monitoring device may be held within piston base 50 by mechanical means, such as a low stick adhesive located between the wearable device and the piston base. In an alternative embodiment, the wearable device may be retained within the housing by a key 35 located in the housing bottom 3. The key 35 aligns with one or more components on the bottom of the wearable device until removal of the housing bottom 3. In an alternative embodiment, one or more springs is provided within the housing having an arm that engages with the wearable device to and a spring portion that is held in place under load by the retractor; upon retraction by the retractor, the spring arms release the wearable device from the piston base. In a further embodiment, a magnet may be placed within a retractor that magnetically engages with a magnetic component within the wearable device, such as a battery. The magnetic connection that secures the wearable device in place within the house may be broken upon retraction of the retractor releasing the wearable device from the housing top 2.

In a further embodiment, as illustrated in FIGS. 14 and 15, the outer surface of housing of the wearable analyte monitoring device 10 comprises a means to prevent rotation of the device within the housing. In one embodiment, dimples or protrusions 161 may be provided to a surface of the wearable device, and mating structures 162, for example, in the form of protrusions or dimples, may be provided to the piston base 50 to hold the wearable device in place. By holding the wearable device in position, the adhesive patch 44 will be held in place as well. In a further embodiment, the piston base comprises vent holes 163 providing an escape path to eliminate the volume of air distal to the piston base that is displaced during insertion, preventing sliding of the adhesive 44 or dimpling of the user's skin for better placement.

In a further embodiment illustrated in FIG. 7A, piston 15 comprises a piston base 50 surrounded by a piston flange 82. The piston flange extends in a proximal direction angled away from the piston base 50 and away from skin of the user. The piston flange 82 further comprises vent holes 83 for displacement of air during insertion.

An alternative embodiment of an analyte sensor applicator is illustrated in FIGS. 4A and 4B. A housing top 2 and housing bottom 3 are provided, and the applicator frame 30 comprises a frame cap 40 that engages with the frame 30. In this embodiment, as illustrated in FIG. 4B the cam assembly is aligned within the applicator frame 30 and beneath the applicator cap 40, and a spring 42 engaged with the cam 25 for activation of the device is confined beneath the frame cap 40. A cam assembly is provided comprising a cam 25, a piston 15 and a retractor 20. In this embodiment, the retractor 20 comprises a rim 46 extending between the top and bottom of the retractor 20 in a gradual slope for slidable engagement with a pin within the cam. During rotational movement of the cam, a cam pin 63 follows the rim 46 of the retractor moving the retractor in a linear direction.

In another embodiment, multiple wedges (not shown) provided on the internal surface of the housing top 2 may engage with slots 33 on the frame cap 40 to lock the component parts and prevent movement of the cam before activation. A wearable analyte monitoring device 11 is secured between the piston 15 and the housing bottom 3 by a chuck 12 that engages with the retractor 20, and a key 35 in the housing bottom 3, prior to activation.

In an alternative embodiment (not shown), a cam assembly is provided comprising the cam and piston, and the retractor is eliminated. In this embodiment, the piston comprises a piston base for holding the wearable device in place against the skin of a user, and a cylindrical portion that moves independently of the bottom portion. The cylindrical portion of the piston engages with the cam. In one embodiment, the piston aligns within the cam, and comprises pins on the external surface to engage with a groove on the internal cam surface; alternatively, the cam aligns within the piston, and a piston pin on the internal cylindrical piston surface engages an external cam groove. The cylindrical piston portion may further comprise a component that engages with the chuck and skin-piercing device for insertion and retraction of the skin-piercing device. In this embodiment, upon activation of the cam, the bottom portion of the piston is pushed to a distal position by the cylindrical piston portion and locked in place holding the wearable device against the skin of a user; the cylindrical portion returns to a proximal position without the base, by slidably engaging with the cam groove securing the skin-piercing device behind the bottom portion of the piston. The cylindrical portion may comprise a 'stop' to engage in a locked proximal position.

In FIGS. 13, 14 and 15, an embodiment of a wearable analyte monitoring device 10 is depicted. The wearable analyte monitoring device 10 may include a wearable housing, an analyte sensor assembly comprising an analyte sensor, an electronics components assembly 81, transducer, and/or battery 79. An adhesive pad 44 optionally attached to the wearable device may further comprise, for example, to the housing bottom 3 to affix the wearable analyte monitoring device 10 to the skin of the user. A plurality of attachment elements 14 may be included within the wearable analyte monitoring system to secure components within the housing of the wearable analyte monitoring device 10.

Effective methods for sterilizing the insertable components (such as, electron beam (E-BEAM) sterilization, or other radiation-based sterilization techniques) may be deleterious to electronic components of the analyte sensor assembly. Thus, the wearable analyte monitoring device 10 may further comprise a sterilized subassembly 56 that is sterilized (for example, by E-BEAM sterilization) prior to further manufacturing of the wearable analyte monitoring component 10. As illustrated in the cross-sectional view of embodiment FIG. 13, a wearable analyte monitoring device 10 comprises a sterile subassembly 55 coupled to the wearable device 10. Insertable portions of the sensor 5 and the lancet 6 are sealed in a small chamber 85, such as a cap 56, which is sterilized prior to incorporation with other components of the wearable device during manufacturing. The lancet may be mated to a loop at one end of the sensor 5 for insertion into the cap, and the other end of the sensor 5 is incorporated within the electronic assembly.

The cap 56 has an opening at a first end to receive the insertable portions into a chamber; the cap opening is sealed and coupled to the wearable device in a manner that a sterile barrier is achieved and maintained. An inert fluid 77 for example, argon gas, may fill the cap displacing environmental oxygen. A sealant is provided to seal the opening of the sterile cap 56 retaining the inert fluid within the chamber 85. The sterility of the insertable components is maintained within the chamber of the cap 56 until inserted into the user.

A method is provided for confirming that a) sterile barrier has been established and b) the sterile barrier is maintained after further assembly. An oxygen sensing component 78 may be applied to, or added to, the chamber 85 of the cap prior to sealing. After assembly, the cap may be interrogated by a light source, such as a UV light source, for the presence of oxygen, an indication of leak in the sterile subassembly through which oxygen is entering the chamber. The oxygen sensing component 78 may comprise an oxygen sensing polymer, polymer laminate, or polymer matrix doped with a luminescent compound, such as an oxygen detecting dye. In some embodiments the dye is a luminescent dye. In some embodiments, the dye is a porphyrin dye, such as platinum tetrakis pentafluorophenyol porphyrin (pT-TFPP). Luminescent dyes (e.g., metallo derivatives) may emit a measurable signal dependent on the amount of oxygen present. In some embodiments a porphyrin dye is configured to reversibly bind to oxygen and to emit light when oxygen is bound. A light source of a compatible or specified frequency may be used to interrogate the sterile cap for the presence or absence of fluorescence behavior that is indicative of the presence of oxygen. Where interrogation signals a breach of the sterile barrier, potential exposure of the insertable components within the chamber to a non-sterile environment may be assumed.

Examples of analyte sensors and oxygen sensing components suitable for use include, but are not limited to materials disclosed in commonly owned U.S. patent application Ser. No. 16/490,118, filed Feb. 28, 2019, entitled ANALYTE SENSORS AND METHODS OF MANUFACTURING ANALYTE SENSORS, and U.S. patent application Ser. No. 16/193,305, entitled SYSTEMS AND METHODS FOR CONTINUOUS HEALTH MONOITORING USING AN OPTO-ENZYMATIC ANALYTE SENSOR", filed Nov. 16, 2018, the contents of which is incorporated by reference herein in its entirety for all purposes.

To facilitate interrogation and visualization, the sterile chamber of the cap 56, or at least a portion of the sterile chamber may comprise a material that is optically transparent to sterilization (e.g., UV sterilization) and/or interrogation technique, such as a clear polycarbonate. In one embodiment, the sterile chamber comprises a one-piece cap that couples to the wearable base 10, for example, by welding or other sealing method, to form a sealed joint 84. To further inhibit gas permeability, at least a portion of the cap 56 may be coated with a non-gas permeable material. Alternatively, the cap may be covered by a second cap comprising a non-gas permeable material that may be coupled to the wearable base 10, or may be coupled directly to the first sterile cap.

In other embodiments the cap may comprise two pieces, wherein a first piece is molded with the wearable base, or integrated into, or coupled with, the wearable base. Where the second cap is molded into the wearable base, a break joint may be provided to facilitate separation of the cap from the wearable base prior to affixing to a user. A second part of a two-part sterile chamber may be coupled to the first part by known means such as welding, adhering, press-fitting, screwing, and the like.

As illustrated in FIGS. 17A and 17B, the analyte sensor applicator housing bottom 3 further comprises an inspection port 54 to inspect the sterile cap 56 for the presence of a sterile environment. The inspection port 54 in the applicator housing aligns with an optically transparent portion of the sterile cap after assembly. The inspection port 54 may be incorporated as hole, or other optically transparent component at any location on the housing that aligns with an optically transparent portion of the sterile subassembly 55. The sterile barrier may also be interrogated through the final packaging materials. In the embodiment of FIGS. 17A and 17B, the inspection port is within the applicator key 35 that secures the sterile subassembly 55 to the housing bottom 3. In the embodiment of FIGS. 17A and 17B, the inspection port 54 is visible through a transparent portion or hole in an applicator key 35 located in the housing bottom 3.

Applicator key 35 also provides a connection between the sterile subassembly 55 and the applicator housing bottom 3. In this embodiment, upon removing the applicator housing bottom 3, the user simultaneously removes the sterile cap 56 of the sterile subassembly 55 exposing the insertable portion of the lancet 6 and sensor 5 for immediate application and insertion of the wearable device. This configuration reduces the number of steps required by a user to prepare the system for insertion. As depicted in FIGS. 17A and 17B, the geometry of the sterile cap may be cone-shaped, and the portion of the key for receiving the sterile cap may be a mating geometry.

In one embodiment, a loose-fitting connection is provided between the housing bottom 3 and the key 35; in one embodiment, the connection between the housing bottom 3 and the key 35 is a pivot. Where misalignment between the housing bottom 3 and the wearable base 10 may place stress on the joint 84 between the sterile cap 56 and the wearable base 10, the loose-fitting connection may facilitate realignment and eliminate stress that may result in a leak or breach of the sterile barrier.

In one embodiment illustrated in FIG. 16A, the portion of the applicator key 35 contained within the applicator housing bottom 3 that connects with the sterile subassembly 55 comprises a cubic shape. In one embodiment, the end of the cap, distal to the wearable device, may have a snap-fit connection 86 with the key 35. When twisting or turning the housing bottom 3 to separate it from the housing top 2, the sterile subassembly 55 contained within the key breaks away from the wearable device and is removed. The sterile subassembly may have one or more flat projections 87 or extensions that engage with the key 35 to facilitate removal upon rotation or twisting of the housing bottom 3.

Once activated and attached to the patient's skin by way of the adhesive pad 44, the analyte sensor assembly may be used for a period of time after which the patient can remove the analyte sensor from the skin by peeling the adhesive pad 44 off of the skin. Removing the analyte sensor assembly also removes the sensing element from the patient's skin.

Analyte sensor applicators disclosed and described herein may be single-use applicators, or reusable applicators that may be used more than one time by a user to transdermally deliver the relevant device components and to attach the device to a user's or patient's skin. In some embodiments, after a wearable analyte monitoring device is removed and disposed of safely by the user, an unused wearable analyte monitoring device can be inserted into the analyte sensor applicator. The user can rewind and activate the applicator to attach a new wearable analyte monitoring device. Accordingly, where the applicator is reusable, the cost of the body wearable medical device (e.g., analyte sensor) is reduced. For subsequent uses of the applicator, a user can purchase new sterile assemblies that include the medical device (transmitter, analyte sensor and skin piercing device) pre-loaded therein.

As will be readily understood by those of skill in the art, embodiments of the disclosed and described applicators, wearable monitoring devices, and sterile assemblies may be designed to other skin piercing elements to transdermally deliver components of a medical device, such as drug delivery cannulas (micro catheters) or other delivery lumens for infusion pumps to deliver, for example, insulin and other therapeutic agents/treatments to a patient. In addition, lancet and other skin-piercing elements may be used with the disclosed and described applicator and sterile assemblies to implant drug eluting implants.

We claim:

1. An analyte sensor applicator for inserting a sensor of a wearable analyte monitoring device, the analyte sensor applicator comprising:
   an applicator housing having an opening at a distal end;
   a skin-piercing device and an insertable portion of the sensor; and
   a cam assembly within the applicator housing, the cam assembly comprising:
      a cylindrical cam comprising:
         a rotational axis;
         an internal cam surface; and
         an external cam surface;
      a piston that engages with the external cam surface, the piston comprising:
         a piston base; and
         a port through the piston base; and

a retractor that engages the internal cam surface and is coupled to the skin-piercing device,
   wherein the cylindrical cam is positioned between the piston and the retractor, wherein the piston moves linearly between a proximal position and a distal position for inserting the sensor with the skin-piercing device, and wherein the retractor moves linearly between a distal position and a proximal position to retract the skin-piercing device through the port to an unexposed position.

2. The analyte sensor applicator of claim 1, wherein the piston further comprises a cylindrical portion that moves independently of the piston base, the cylindrical portion engages with the cylindrical cam and the skin-piercing device.

3. The analyte sensor applicator of claim 2, wherein upon activation of the cylindrical cam, the piston base is pushed to the distal position by the cylindrical portion and locked in place and the cylindrical portion returns to the proximal position without the piston base.

4. The analyte sensor applicator of claim 3, wherein the cylindrical portion further comprises a stop to engage the cylindrical portion in the proximal position.

5. The analyte sensor applicator of claim 1, wherein the external cam surface comprises a groove and the piston comprises a pin that rides in the groove.

6. The analyte sensor applicator of claim 1, wherein the internal cam surface comprises a groove and the retractor comprises a pin that rides in the groove.

7. The analyte sensor applicator of claim 1, wherein the retractor comprises a groove or rim on an external surface and the cylindrical cam comprises a pin that follows the groove or rim of the retractor.

8. The analyte sensor applicator of claim 7, wherein the piston comprises one or more internal pins that engage with one or more holes within the retractor to inhibit rotational movement of the retractor relative to the piston.

9. A system comprising:
   the analyte sensor applicator of claim 1; and
   the wearable analyte monitoring device comprising:
      an electronics assembly and sensor components coupled on a proximal side of the wearable analyte monitoring device; and
      an adhesive component on a distal side of the wearable analyte monitoring device to adhere the wearable analyte monitoring device to a user,
   wherein insertable portions of the skin-piercing device and the sensor project from the distal side.

10. The analyte sensor applicator of claim 1, wherein the skin-piercing device is a lancet.

11. The analyte sensor applicator of claim 1, wherein the skin-piercing device is a cannula.

12. The analyte sensor applicator of claim 1, wherein the piston comprises a disc shaped piston base that engages with the wearable analyte monitoring device.

13. The analyte sensor applicator of claim 1, wherein the insertable portion of the skin-piercing device is retracted through the port.

14. The analyte sensor applicator of claim 1, wherein the retractor is configured to move independently of the piston.

15. The analyte sensor applicator of claim 1, wherein when the retractor moves to its proximal position, and the piston base is configured to remain in a fixed distal position, after insertion.

16. The analyte sensor applicator of claim 1, wherein the retractor engages with the internal cam surface for linear movement along an insertion axis upon rotation of the cylindrical cam.

17. The analyte sensor applicator of claim 1, wherein the cylindrical cam engages with a retractor rim for linear movement of the retractor along an insertion axis upon rotation of the cylindrical cam.

18. A system comprising:

the analyte sensor applicator of claim 1; and a sterile subassembly comprising:

a cap;

distal portions of the skin-piercing device and the sensor inserted into the cap and held within a first sterile environment within the cap;

a component for visually detecting a sterile environment within the cap; and an inspection port in the applicator housing for detecting the sterile environment.

19. The system of claim 18, wherein the cap is filled with an inert fluid and the component for visually detecting the sterile environment is a luminescent material.

20. The analyte sensor applicator of claim 1, wherein the retractor is coupled to the skin-piercing device via an applicator chuck.

\* \* \* \* \*